(12) United States Patent
Popovic

(10) Patent No.: US 10,667,872 B2
(45) Date of Patent: *Jun. 2, 2020

(54) ENDOSCOPY-GUIDED DEPLOYMENT OF VESSEL PUNCH

(71) Applicant: KONINKLIJKE PHILIPS N.V., Eindhoven (NL)

(72) Inventor: Aleksandra Popovic, Boston, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 158 days.

This patent is subject to a terminal disclaimer.

(21) Appl. No.: 15/699,625

(22) Filed: Sep. 8, 2017

(65) Prior Publication Data

US 2018/0055585 A1  Mar. 1, 2018

Related U.S. Application Data

(63) Continuation of application No. 13/877,475, filed as application No. PCT/IB2011/054354 on Oct. 4, 2011, now Pat. No. 9,788,901.

(60) Provisional application No. 61/391,143, filed on Oct. 8, 2010.

(51) Int. Cl.

| A61B 1/00 | (2006.01) |
| A61B 34/30 | (2016.01) |
| A61B 17/3205 | (2006.01) |
| A61B 1/313 | (2006.01) |
| A61B 17/00 | (2006.01) |
| A61B 90/00 | (2016.01) |

(52) U.S. Cl.
CPC ............. *A61B 34/30* (2016.02); *A61B 1/00* (2013.01); *A61B 17/32053* (2013.01); *A61B 1/0014* (2013.01); *A61B 1/00087* (2013.01); *A61B 1/00149* (2013.01); *A61B 1/313* (2013.01); *A61B 2017/0034* (2013.01); *A61B 2090/3614* (2016.02)

(58) Field of Classification Search
CPC ... A61B 1/00; A61B 1/00149; A61B 1/00087; A61B 1/313; A61B 1/0014; A61B 17/32053; A61B 2090/3614; A61B 2017/0034
See application file for complete search history.

(56) References Cited

U.S. PATENT DOCUMENTS

| 4,793,326 A | 12/1988 | Shishido |
| 4,909,782 A | 3/1990 | Semm |
| 4,998,282 A * | 3/1991 | Shishido ................ A62B 99/00 381/124 |
| 5,403,338 A | 4/1995 | Milo |
| 5,476,473 A | 12/1995 | Heckele |
| 5,702,420 A | 12/1997 | Sterling |
| 5,820,623 A | 10/1998 | Ng |
| 6,059,719 A | 5/2000 | Yamamoto |

(Continued)

FOREIGN PATENT DOCUMENTS

| CN | 2580910 Y | 10/2003 |
| CN | 101301220 A | 11/2008 |

*Primary Examiner* — Timothy J Neal

(57) ABSTRACT

A robotic punch system employs a robot unit and a control unit. The robot unit includes a robot and an endoscopic punch mounted to the robot. The endoscopic punch includes a calibrated spatial alignment of an endoscope and a punch. The control unit commands the robot for deploying the endoscopic punch in executing a puncture of an anatomical tissue.

12 Claims, 7 Drawing Sheets

(56) References Cited

U.S. PATENT DOCUMENTS

| | | |
|---|---|---|
| 6,451,027 B1 | 9/2002 | Cooper |
| 6,770,081 B1 | 8/2004 | Cooper |
| 6,827,712 B2 | 12/2004 | Tovey |
| 6,840,900 B2 | 1/2005 | Smith |
| 6,908,427 B2 | 6/2005 | Fleener |
| 7,497,826 B2 | 3/2009 | Ouchi |
| 8,529,433 B2 | 9/2013 | Kawano |
| 9,788,901 B2 * | 10/2017 | Popovic .................. A61B 1/00 |
| 2002/0177865 A1 | 11/2002 | McIntosh |
| 2004/0243109 A1 | 12/2004 | Tovey |
| 2005/0256371 A1 | 11/2005 | Schara |
| 2007/0260113 A1 | 11/2007 | Otawara |
| 2008/0103357 A1 | 5/2008 | Zeiner |
| 2009/0228020 A1 | 9/2009 | Wallace |
| 2009/0275798 A1 | 11/2009 | Naito |
| 2010/0113873 A1 | 5/2010 | Suzuki |
| 2010/0179381 A1 | 7/2010 | Kawano |
| 2011/0113873 A1 | 5/2011 | Suzuki |
| 2013/0325028 A1 | 12/2013 | Popovic |

\* cited by examiner

ENDOSCOPY-GUIDED DEPLOYMENT OF VESSEL PUNCH

This application is a continuation application under 37 C.F.R. § 1.53(b)(1) of commonly owned U.S. patent application Ser. No. 13/877,475 (the parent application) to Popovic entitled "ENDOSCOPY-GUIDED DEPLOYMENT OF VESSEL PUNCH" filed on 20 Aug. 2013. The present application claims priority under pre-AIA 35 U.S.C. § 120 to U.S. patent application Ser. No. 13/877,475, the disclosure of which is hereby incorporated by reference in its entirety.

The parent application claims priority from International Patent Application PCT/IB2011/054354 filed on Oct. 4, 2011. International Patent Application PCT/IB2011/054354 in turn claims priority from U.S. Provisional Application 61/391,143. This application claims priority from International Patent Application PCT/IB2011/054354, and under pre-AIA 35 U.S.C. § 119(e) from U.S. Provisional Application 61/391,143, the disclosures of which are hereby incorporated by reference in their entirety.

The present invention generally relates to the use of punch devices during a surgical procedure, particularly a minimally invasive surgical procedure (e.g., a minimally invasive coronary bypass grafting surgery). The present invention specifically relates to a robotic deployment of a vessel punch and an endoscope having a known spatial relationship.

A vessel punch is a disposable device used to make a clean hole in a blood vessel. A vessel punch is used in various cardiovascular procedures to facilitate attachment of a graft vessel to a base vessel. For example, in coronary artery bypass grafting, a vessel punch may be used for attachment of a graft artery to the aorta to facilitate blood flow through the graft and bypass the diseased artery.

Commercially available punch devices deploy vessel punch and a spring/release mechanism to allow quick release of a needle-like device. The spring mechanism provides a surgeon with much higher force and speed as compared to a manually operated needle. After a small linear incision in the aortic wall is made using a scalpel, the anvil of punch is placed in the incision. In the next step, the punch is released to open the hole.

Typically, the tip of a punch device is approximately 2.5-5 mm diameter. The body of the device is usually 10 mm in diameter for minimally invasive procedures and approximately 20 mm for open-heart surgery. In minimally invasive procedures, the punch is introduced through one of two instrument ports, leaving only one surgical instrument available to the surgeon. For example, as shown in FIG. 1, a punch device 21 and a surgical instrument 22 are introduced through instrument ports of a chest 20 while an endoscope 23 is introduced through a viewing port of chest 20 for visually monitoring the surgical area.

However, with this arrangement, punch device 21 being through the instrument port into the chest 20 as opposed to another surgical instrument may significantly impair a surgeon's ability to act in moments following the puncture. For example, high pressure of blood in the aorta may cause bleeding that should be immediately managed by the surgeon and surgical instrument 21 may be insufficient to manage the blood.

Most of available punch devices are significantly larger than working channels of endoscopes and therefore cannot be deployed through the working channels of endoscopes as a resolution to the arrangement of FIG. 1. Specifically, the large size of punch devices originates in the design of the spring/release mechanism that cannot be made smaller than 5 mm in view of the fact that the spring/release mechanism is operated directly by the surgeon. Furthermore, the surgeon cannot directly deploy the needle without the spring/release mechanism since the forces and speeds required are beyond human capabilities. Furthermore, punch devices that can be used in minimally invasive procedures have to be deployed through an instrument port, causing above described problems.

The present invention provides systems and methods of robotic deployment of an endoscope and a punch having a known spatial relationship. For example, the punch may be deployed through a working channel of an endoscope or through a separate fixture parallel to the endoscope.

One form of the present invention is a robotic punch system employing a robot unit and a control unit. The robot unit includes a robot and an endoscopic punch mounted to the robot. The endoscopic punch includes a calibrated spatial alignment of an endoscope and a punch. The control unit commands the robot for deploying the endoscopic punch in executing a puncture of an anatomical tissue.

A second form of the present invention is a robotic punch method involving a mounting of an endoscopic punch to a robot, wherein the endoscopic punch includes a calibrated spatial alignment of an endoscope and a punch. The robotic punch method further involves an operation of the robot to place the endoscopic punch through a target puncture site on an anatomical tissue.

The foregoing forms and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

Figure 1:
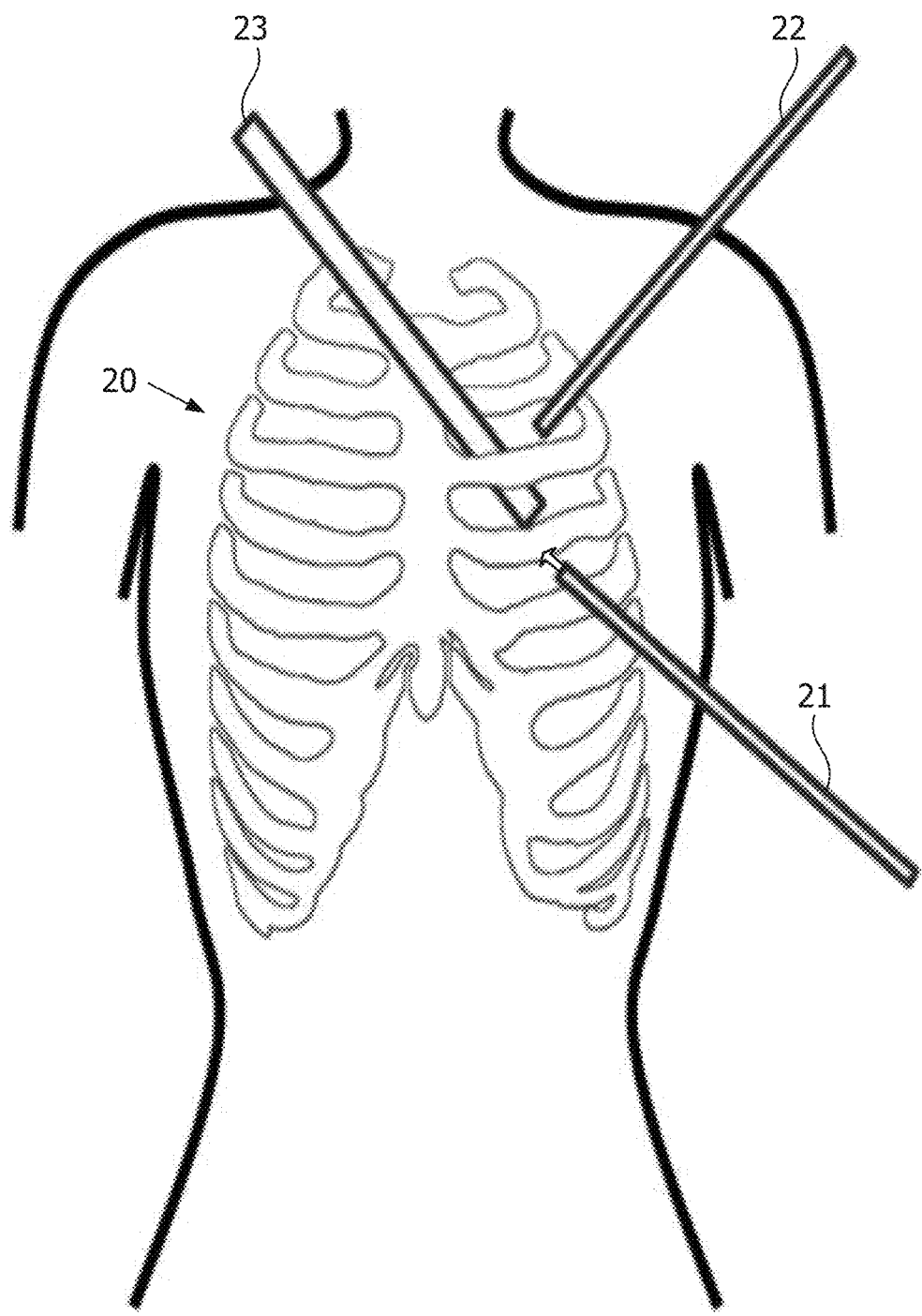
FIG. 1 illustrates an exemplary embodiment of a minimally invasive surgical procedure using a punch device as known in the art.
Figure 2:
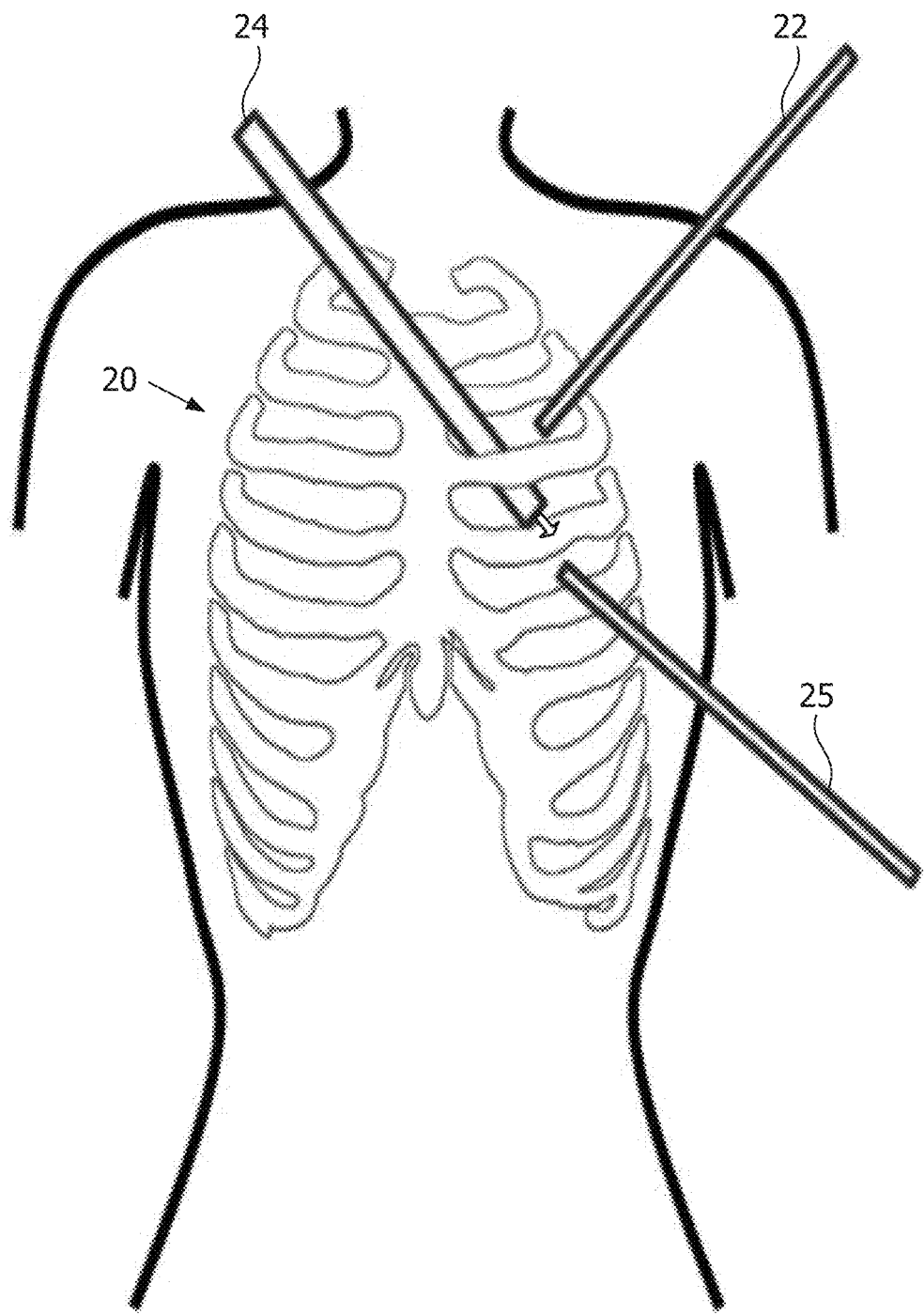
FIG. 2 illustrates an exemplary embodiment of a minimally invasive surgical procedure using an endoscopic punch device in accordance with the present invention.

As shown in FIG. 2, the present invention provides an endoscopic punch 24 that allows two (2) surgical instruments 22 and 25 to be introduced through instrument ports of a chest 20 prior to a puncture or piercing of an anatomical tissue (not shown) during a minimally invasive surgical procedure. Specifically, as will be further explained herein, endoscopic punch 24 is deployed in a manner that facilitates an endoscopic view of a target puncture site on an anatomical tissue followed by a puncture or piercing of the target puncture site. As such, surgical instruments 22 and 25 are immediately available for a surgeon to implement any necessary course of action due to the puncture or piercing of the target puncture site.

For purposes of the present invention, an "endoscopic punch" is broadly defined herein as any device having a calibrated spatial alignment between an endoscope and a punch, the term "calibrated" is broadly defined herein as a precise measurement, and the term "alignment" encompasses parallel and non-parallel alignments between the endoscope and the punch.

Also, for purposes of the present invention, an "endoscope" is broadly defined herein as any device structurally configured with ability to image from inside a body. Examples of an endoscope include, but are not limited to, any type of scope, flexible or rigid (e.g., endoscope, arthroscope, bronchoscope, choledochoscope, colonoscope, cystoscope, duodenoscope, gastroscope, hysteroscope, laparoscope, laryngoscope, neuroscope, otoscope, push enteroscope, rhinolaryngoscope, sigmoidoscope, sinuscope, thorascope, etc.) and any device similar to a scope that is equipped with an image system (e.g., a nested cannula with imaging). The imaging is local, and surface images may be obtained optically with fiber optics, lenses, and miniaturized (e.g. CCD based) imaging systems.

Further, for purposes of the present invention, a "punch" is broadly defined herein as any article or device structurally configured for puncturing or piercing anatomical tissue exclusive of a spring/release mechanism as known in the art. In practice, the anatomical tissue may have an incision for facilitating the puncturing or piercing of the anatomical tissue by the punch.

FIGS. 3-10 will now be described herein to facilitate an understanding of an endoscopic punch of the present invention.

Figure 3:
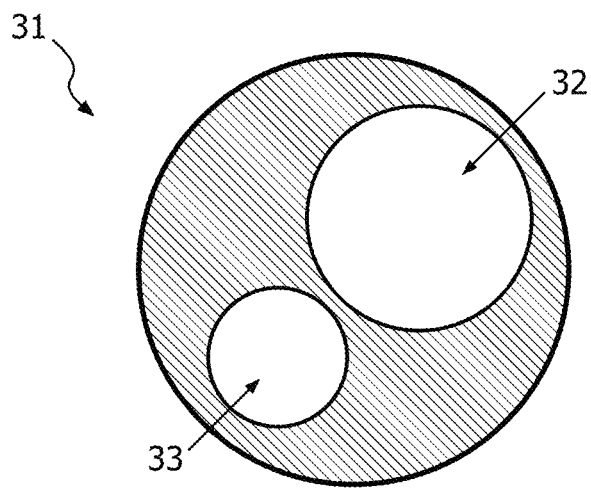
FIG. 3 illustrates a cross-sectional view of an endoscope as known in the art.
Figure 4:
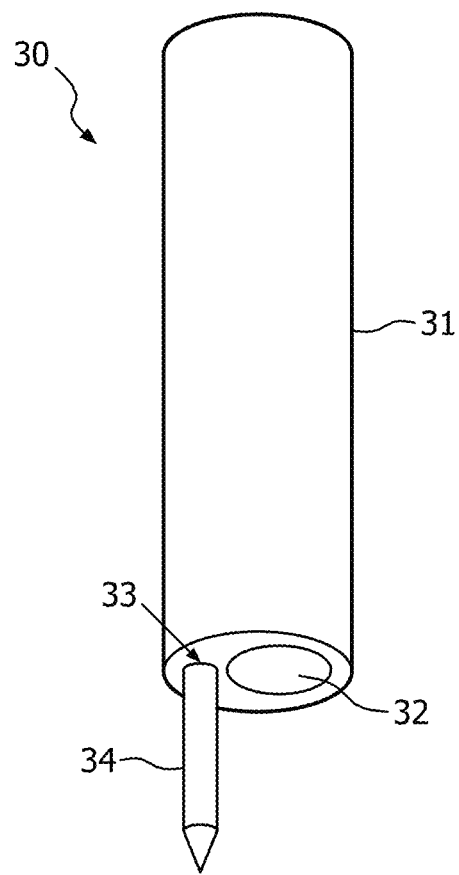
FIG. 4 illustrates a longitudinal perspective view of one exemplary embodiment of an endoscopic punch device in accordance with the present invention.

Referring to FIGS. 3 and 4, an endoscopic punch 30 includes an endoscope 31 having a viewing channel 32 and a working channel 33 as known in the art. A punch 34 is attached to a distal end of the working channel 33 as shown in FIG. 4 and has a calibrated spatial alignment with viewing channel 32. In one embodiment of endoscopic punch 30, a tip of punch 34 is spatially aligned with a distal lens (not shown) of viewing channel 32 and a distance between the tip of the punch 34 and a center of the lens is precisely measured. In another embodiment, punch 34 is inserted through working channel 33 and a calibrated spatial alignment of the tip punch 34 and viewing channel 32 is obtained for the punch operation. In this embodiment, punch 34 may be removed after the punch operation has been performed.

In practice, punch 34 may be partially or entirely within a field of view of viewing channel 32.

Figure 5:
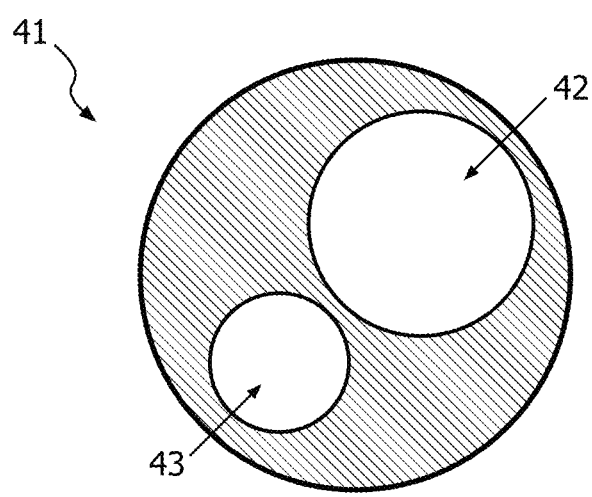
FIG. 5 illustrates a cross-sectional view of an endoscopic mount in accordance with the present invention.
Figure 6:
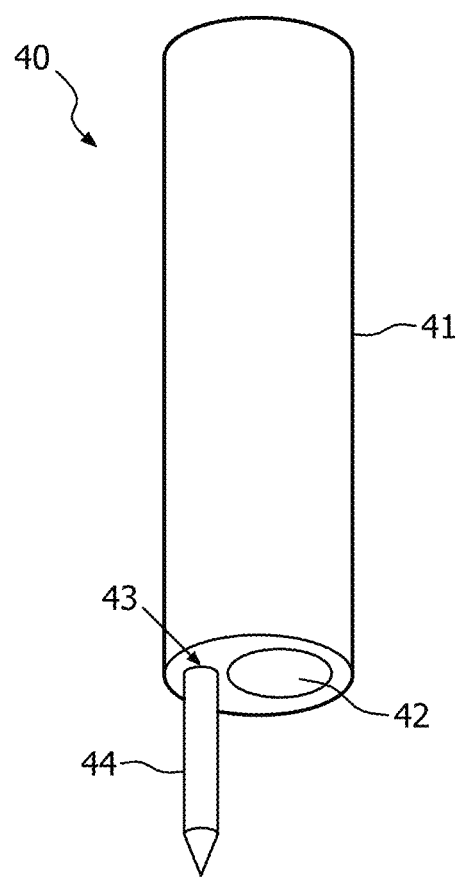
FIG. 6 illustrates a longitudinal perspective view of one exemplary embodiment of an endoscopic punch device in accordance with the present invention.

Referring to FIGS. 5 and 6, an endoscopic punch 40 includes an endoscopic mount 41 having an endoscope 42 and a punch channel 43. A punch 44 is attached to a distal end of the punch channel 43 as shown in FIG. 6 and has a calibrated spatial alignment with endoscope 42. In one embodiment of endoscopic punch 40, a tip of punch 44 is spatially aligned with a distal lens (not shown) of endoscope 42 and a distance between the tip of the punch 44 and a center of the lens is precisely measured.

In practice, punch 44 may be partially or entirely within a field of view of endoscope 42. Further, while endoscope 42 is shown as having a viewing channel exclusively, in practice endoscope 42 may also have a working channel located within endoscopic mount 41.

Figure 7:
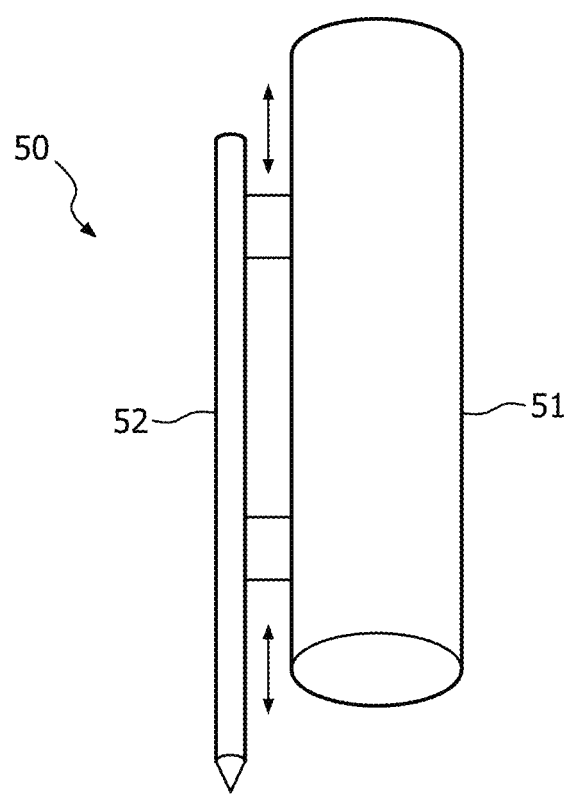
FIG. 7 illustrates a longitudinal perspective view of a third exemplary embodiment of an endoscopic punch device in accordance with the present invention.
Figure 8:
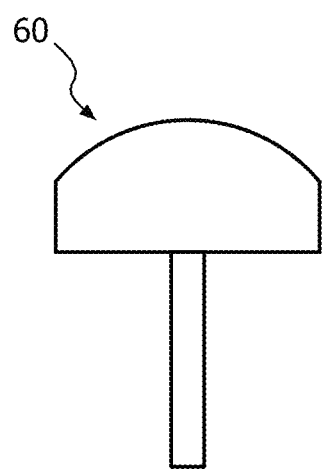
FIGS. 8-10 illustrate various exemplary embodiments of a punch in accordance with the present invention.
Figure 9:
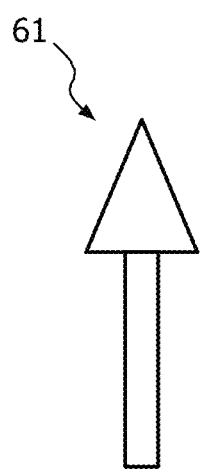
Figure 10:
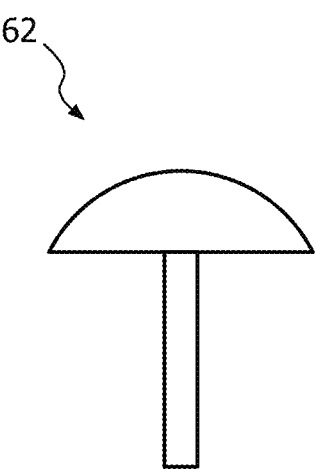

Referring to FIG. 7, an endoscopic punch 50 includes an endoscope 51 and a punch 52 parallel mounted to endoscope 51. In the illustrated embodiment of endoscopic punch 50, punch 52 is movably mounted to endoscope 51 as indicated by the arrows shown in FIG. 7 whereby punch 52 may be moved to a working position having a calibrated spatial alignment with endoscope 51 as shown in FIG. 7. Alternatively, punch 52 may be permanently mounted in the working position. For either embodiment, a tip of punch 52 may be spatially aligned with a distal lens (not shown) of endoscope 51 and a distance between the tip of the punch 52 and a center of the lens is precisely measured.

In practice, punch 52 may be partially or entirely within a field of view of endoscope 51. Further, while endoscope 51 is shown as having a viewing channel exclusively, in practice endoscope 51 may also have a working channel.

FIGS. 4, 6 and 7 illustrate punches having a sharp needle like tip. In practice, the present invention does not impose any restrictions or limitations to the structural design of a tip of a punch. For example, FIGS. 8-10 respectively illustrate punches 60-62 of varying tip designs.

FIGS. 11-14 will now be described herein to facilitate an understanding of a robotic punch system of the present invention.

Figure 11:
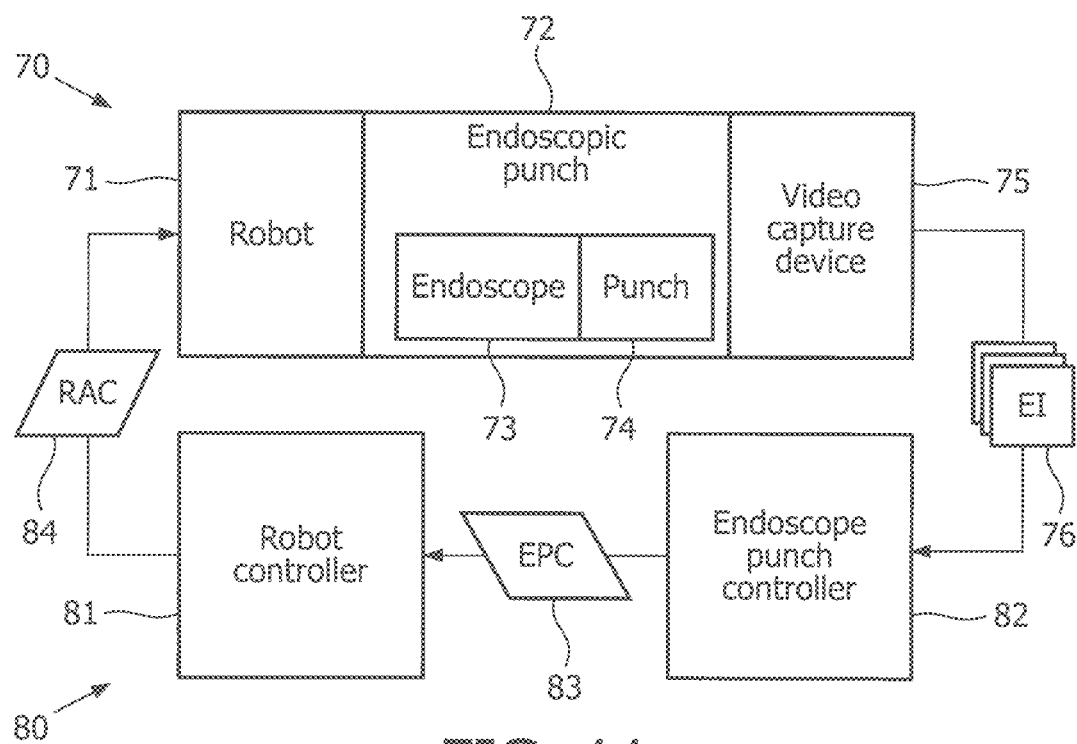
FIG. 11 illustrates an exemplary embodiment of a robotic punch system in accordance with the present invention.

As shown in FIG. 11, a robotic punch system of the present invention employs a robot unit 70 and a control unit 80 for any endoscopic procedure involving an endoscopic imaging of an anatomical region of a body, human or animal. Examples of such endoscopic procedures include, but are not limited to, minimally invasive cardiac surgery (e.g., coronary artery bypass grafting or mitral valve replacement).

Robot unit 70 includes a robot 71, an endoscope punch 72 rigidly attached to robot 71 and a video capture device 75 attached to the endoscopic punch 72.

Robot 71 is broadly defined herein as any robotic device structurally configured with motorized control of one or more joints for maneuvering an end-effector as desired for the particular endoscopic procedure. In practice, robot 71 may have four (4) degrees-of-freedom, such as, for example, a serial robot having joints serially connected with rigid segments, a parallel robot having joints and rigid segments mounted in parallel order (e.g., a Stewart platform known in the art) or any hybrid combination of serial and parallel kinematics. Robot 71 may also be any variation of a continuous robot consisting of a series of short rigid or flexible segments attached with a plurality of joints (e.g., a snake robot or an inchworm robot).

In practice, endoscopic punch 72 is mounted to the end-effector of robot 71. A pose of the end-effector of robot 71 is a position and an orientation of the end-effector within a coordinate system of robot 71 actuators. With endoscopic punch 72 mounted to the end-effector of robot 71, any given pose of the field-of-view of endoscopic punch 72 within an anatomical region corresponds to a distinct pose of the end-effector of robot 71 within the robotic coordinate system. Consequently, each individual endoscopic image of an anatomical region generated by endoscopic punch 72 may be linked to a corresponding pose of endoscopic punch 72 within the anatomical region.

Video capture device 75 is broadly defined herein as any device structurally configured with a capability to convert an endoscopic video signal from endoscopic punch 72 into a computer readable temporal sequence of endoscopic image ("EI") 76. In practice, video capture device 75 may employ a frame grabber of any type for capturing individual digital still frames from the endoscopic video signal.

Still referring to FIG. 11, control unit 80 includes a robot controller 81 and an endoscope controller 82.

Robot controller 81 is broadly defined herein as any controller structurally configured to provide one or more robot actuator commands ("RAC") 84 to robot 71 as known in the art for controlling a pose of the end-effector of robot 71 as desired for the endoscopic procedure. More particularly, robot controller 81 converts endoscope position commands ("EPC") 83 from endoscope controller 82 into robot actuator commands 84. For example, endoscope position commands 83 may indicate an endoscopic path leading to desired 3D position of a field-of-view of endoscopic punch 72 within an anatomical region whereby robot controller 81 converts command 83 into commands 84 including an actuation current for each motor of robot 71 as needed to move endoscopic punch 72 to the desired 3D position.

Endoscope controller 82 is broadly defined herein as any controller structurally configured for implementing an endoscopic guidance method as known in the art. For example, endoscope controller 82 may implement a master-slave control method or a visual servoing method that utilizes endoscopic images 76.

Figure 12:
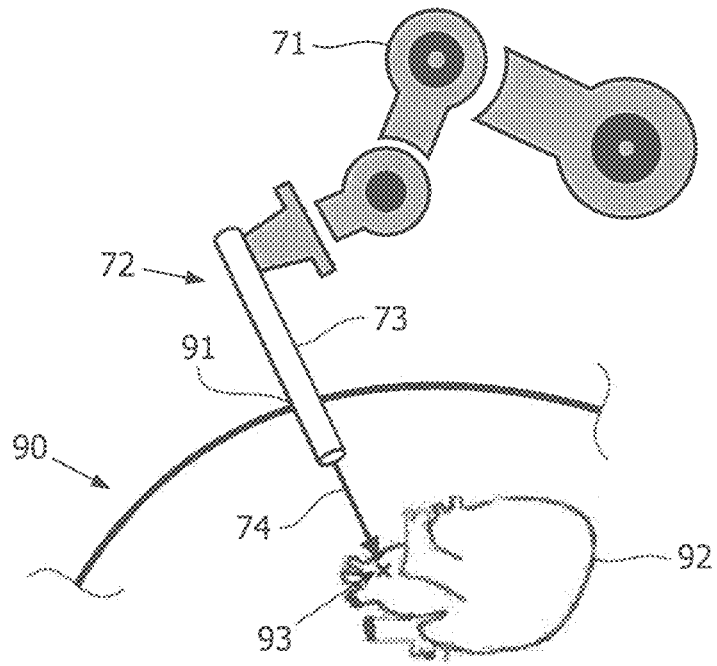
FIG. 12 illustrates an exemplary example a minimally invasive surgical procedure using the robotic punch system in accordance with the present invention.

Generally, in operation as shown in FIG. 12, controllers 81 and 82 collectively operate robot 71 in maneuvering endoscopic punch 72 after insertion of endoscopic punch 72 within an insertion port 91 of a body 90. Preferably, the kinematics of robot 71 facilitates a pivoting of endoscopic punch 72 around an insertion port 91 and facilitates a linear motion of robot 71 along a main axis of endoscope 73. As such, endoscopic punch 72 may be rotated and translated as needed to reach a target puncture site 93 on a heart 92. And, upon reaching the target puncture site 93, controllers 81 and 82 operate robot 71 in deploying endoscopic punch 72 in puncturing an incision of heart 92 at the target puncture site 93.

A description of flowchart 100 will now be provided herein to facilitate a further understanding of an operation of the robotic punch system of the present invention.

Figure 13:
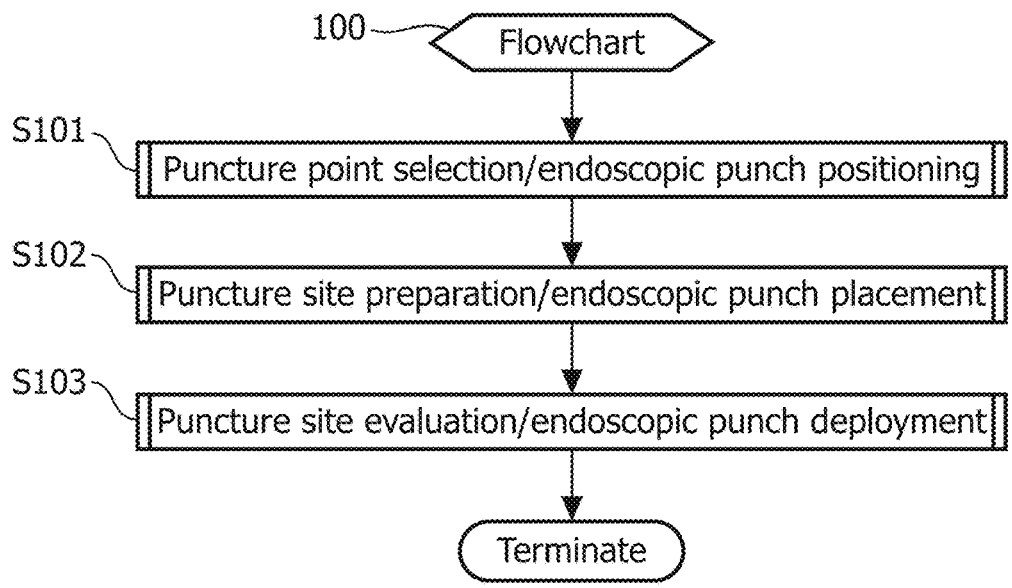
FIG. 13 illustrates a flowchart representative of an exemplary embodiment of a robotic punch method in accordance with the present invention.
Figure 14:
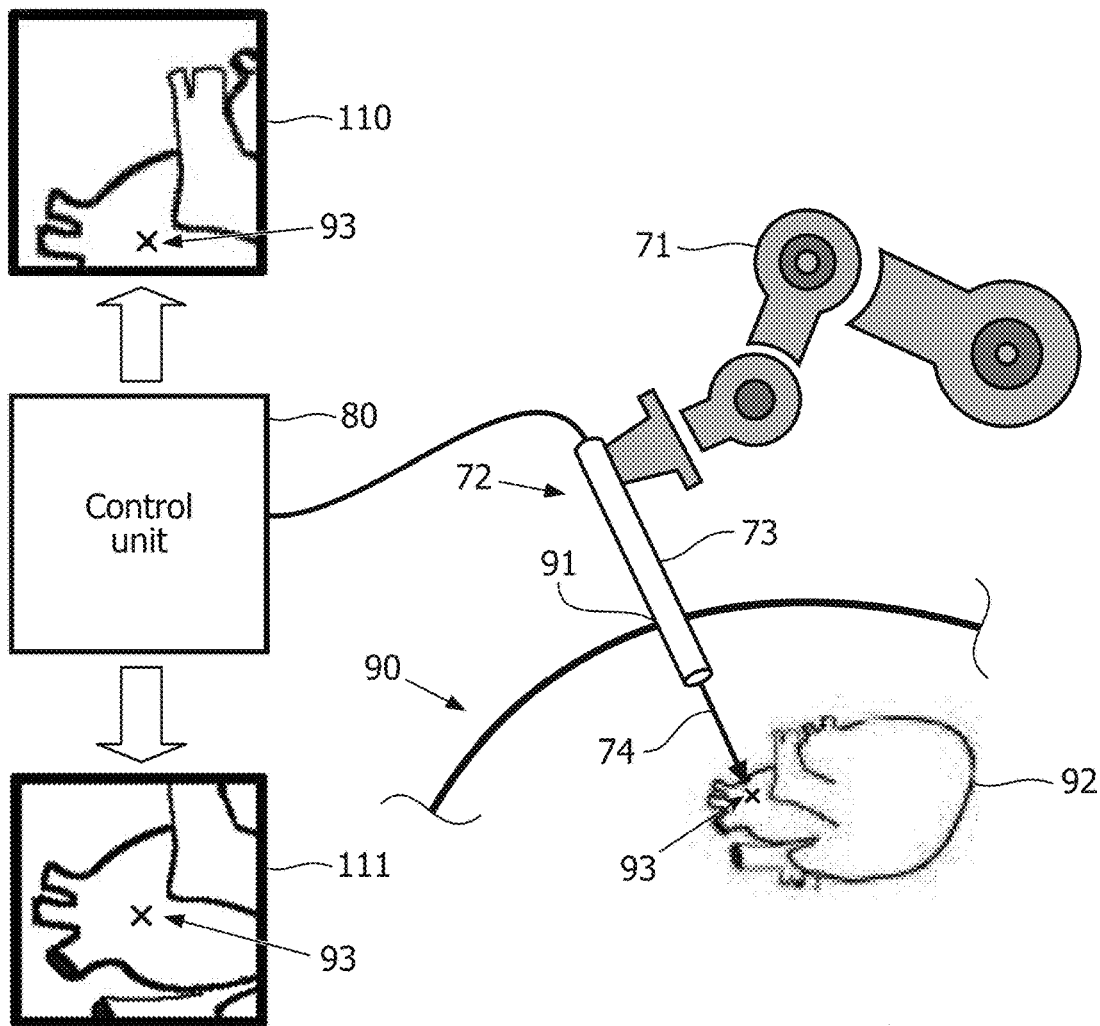
FIG. 14 illustrates an exemplary minimally invasive surgically procedure implementation of the flowchart shown in FIG. 13.

Referring to FIGS. 13 and 14, a stage S101 of flowchart 100 encompasses a selection of target puncture site 93 on heart 92 and a positioning of endoscopic punch 72 whereby punch 74 is adjacent but not touching target puncture site 93. In one embodiment of stage S101, after a surgeon has setup the necessary ports (e.g., port 91) for endoscopic punch 72 and two (2) surgical instruments (not shown) and performed any other necessary surgical tasks, the surgeon may view endoscopic images 76 (FIG. 11) to manually guide endoscopic punch 72 in a direction of target puncture site 93.

Alternatively, the surgeon may select target puncture site 93 in a current endoscopic view of heart 92, such as, for example, a displayed view 110 of heart 92 as shown in FIG. 14. From the selection, control unit 80 will operate robot 71 in guiding endoscopic punch 72 to target puncture site 93.

A stage S102 of flowchart 100 encompasses a preparation of target puncture site 93 for a placement of punch 74 on target puncture site 93. In one embodiment of stage S102, the surgeon prepares target puncture site 93 with a linear incision and control unit 80 operates robot 71 in placing punch 74 at target puncture site 93.

A stage S103 of flowchart 100 encompasses an evaluation of punch 74 at target puncture site 93, such as, for example, an evaluation of a displayed view of 111 of target puncture site 93. In view of the evaluation, the surgeon may command control unit 80 in adjusting the positioning of punch 74 at target puncture site 93. Regardless of whether position adjustments were implemented, endoscopic punch 72 is deployed upon the surgeon ascertaining the position of punch 74 at target puncture site 93 is acceptable. In one embodiment of stage S103, control unit 80 operates robot 71 in moving endoscopic punch 72 along the axis of endoscope 73 whereby punch 74 is "slowly" placed within the incision of target puncture site 93.

Upon termination of flowchart 100, the two (2) surgical instruments may be utilized as needed to address any issues with the puncturing of heart 92.

From the description of FIGS. 1-14 herein, those having ordinary skill in the art of the present invention will appreciate the numerous benefits of the present invention including, but not limited to, an application of the present invention to any type of endoscopic surgery involving the incision and follow-up puncture of tissue. Furthermore, those having skill in the art of the present invention will appreciate numerous advantages of the robotic punch system of the present invention including, but not limited to, a use of a sufficient type and quantity of surgical instruments to remain inside of the patient's body during puncture allowing a rapid response to possible complications, a significant reduction in the size of the punch device in view of an omission of conventional spring/release mechanism in the robotic punch system, visual guidance for puncture allows precise positioning of the hole, and a surgical control over depth and speed of the punch which is uncontrollable in spring-loaded punches.

Although the present invention has been described with reference to exemplary aspects, features and implementations, the disclosed systems and methods are not limited to such exemplary aspects, features and/or implementations. Rather, as will be readily apparent to persons skilled in the art from the description provided herein, the disclosed systems and methods are susceptible to modifications, alterations and enhancements without departing from the spirit or scope of the present invention. Accordingly, the present invention expressly encompasses such modification, alterations and enhancements within the scope hereof.

The invention claimed is:

1. An endoscopic punch comprising:
   an endoscopic mount having an endoscope and a working channel disposed therein; and
   a punch comprising a distal end, the punch partially disposed within the working channel of the endoscopic mount and fixedly extending beyond the distal end of the endoscopic mount, wherein the distal end of the punch is configured to remain fixed in location relative to the endoscope mount upon application of an external force.

2. The endoscopic punch of claim 1, wherein the endoscope and the punch have a measured spatial alignment within the endoscope mount.

3. The endoscopic punch of claim 1, wherein the distal end of the punch is entirely in a field of view of the endoscope.

4. The endoscopic punch of claim 1, wherein the punch does not have a spring-release mechanism.

5. The endoscopic punch of claim 1, wherein the punch has a tip at the distal end, and the tip is adapted to pierce tissue.

6. The endoscopic punch of claim 1, wherein the punch is only partially in a field of view of the endoscope.

7. A robotic punch system comprising:
- an endoscopic mount having an endoscope and a working channel disposed therein;
- a punch comprising a distal end, the punch partially disposed within the working channel of the endoscopic mount and fixedly extending beyond the distal end of the endoscopic mount, wherein the distal end of the punch is configured to remain fixed in location relative to the endoscope mount upon application of an external force does not comprise moving elements;
- a robot comprising an end-effector and robotic motors that move a position of the end-effector, the endoscopic mount being attached to the end-effector; and
- a control circuit that generates actuation currents for each of the robot motors and conveys corresponding actuation currents to each of the robot motors so as to move the punch to a desired three-dimensional location.

8. The robotic punch system of claim 7, wherein the endoscope and the punch have a measured spatial alignment within the endoscope mount.

9. The robotic punch system of claim 7, wherein the punch is in a field of view of the endoscope.

10. The robotic punch system of claim 7, wherein the punch does not have a spring-release mechanism.

11. The robotic punch system of claim 10, wherein the punch has a tip at a distal end, and the tip is adapted to pierce tissue.

12. The robotic punch system of claim 7, wherein the robot has four (4) degrees of freedom.

* * * * *